| United States Patent [19] | [11] | 4,165,337 |
|---|---|---|
| Yoshinaka et al. | [45] | Aug. 21, 1979 |

[54] PROCESS FOR PRODUCING PHTHALOYL DICHLORIDES OF HIGH PURITY

[75] Inventors: Shigeo Yoshinaka; Masaharu Doya; Seiji Uchiyama; Sadao Nozaki, all of Niigata, Japan

[73] Assignee: Mitsubishi Gas Chemical Company, Inc., Tokyo, Japan

[21] Appl. No.: 844,814

[22] Filed: Oct. 25, 1977

[30] Foreign Application Priority Data

Oct. 25, 1976 [JP] Japan .................................. 51/127925

[51] Int. Cl.² ............................................. C07C 51/58
[52] U.S. Cl. ....................... 260/544 D; 204/158 HA; 204/163 R
[58] Field of Search ................ 260/544 D; 204/163 R, 204/158 HA

[56] References Cited

U.S. PATENT DOCUMENTS

| 4,029,560 | 1/1977 | Yoshinaka et al. | .............. 260/544 D |
| 4,048,033 | 9/1977 | Yoshinaka et al. | .............. 260/544 D |

FOREIGN PATENT DOCUMENTS 1196636  7/1965  Fed. Rep. of Germany ........... 260/544
946491  1/1964  United Kingdom ..................... 260/544

Primary Examiner—Gerald A. Schwartz
Attorney, Agent, or Firm—Wenderoth, Lind & Ponack

[57] ABSTRACT

A batchwise or continuous process for producing isophthaloyl dichloride or terephthaloyl dichloride having a high purity which comprises, in combination, (1) a first step of producing $\alpha,\alpha,\alpha,\alpha',\alpha',\alpha'$-hexachloroxylene by reacting meta- or para-xylene with chlorine under the irradiation of ultraviolet-containing rays, the reaction being carried out in the presence of, as a solvent, $\alpha,\alpha,\alpha,\alpha',\alpha',\alpha'$-hexachloroxylene added at the outset of the reaction; (2) a second step of producing isophthaloyl dichloride or terephthaloyl dichloride by reacting the $\alpha,\alpha,\alpha,\alpha',\alpha',\alpha'$-hexachloroxylene obtained in the first step with isophthalic acid or terephthalic acid; and (3) a third step of purifying the isophthaloyl dichloride or terephthaloyl dichloride obtained in the second step by dissolving the isophthaloyl dichloride or terephthaloyl dichloride in 0.3 to 6 parts by weight; per part by weight of the phthaloyl dichloride, of $C_6$–$C_{10}$ aliphatic hydrocarbon solvent, and cooling the solution to a temperature of the specified range thereby to recrystallize the phthaloyl dichloride.

4 Claims, No Drawings

PROCESS FOR PRODUCING PHTHALOYL DICHLORIDES OF HIGH PURITY

BACKGROUND OF THE INVENTION

This invention relates to a process for producing isophthaloyl dichloride or terephthaloyl dichloride of high purity.

Various methods have been suggested for producing the isophthaloyl dichloride or terephthaloyl dichloride, and among them, a method for producing isophthaloyl dichloride or terephthaloyl dichloride which comprises chlorinating m-xylene or p-xylene or a compound resulting from the partial chlorine-substitution of its methyl groups to form $\alpha,\alpha,\alpha,\alpha',\alpha',\alpha'$-hexachloroxylene, and reacting the resulting hexachloroxylene with isophthalic acid or terephthalic acid is especially advantageous from an economic standpoint.

The reactions in this method are schematically shown by the following reaction equations (I) and (II).

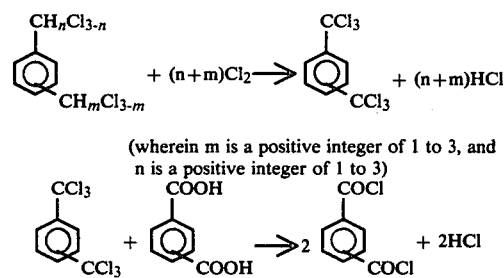

(wherein m is a positive integer of 1 to 3, and n is a positive integer of 1 to 3)

It is also known to produce isophthaloyl dichloride or terephthaloyl dichloride by reacting hexachloroxylene with a monocarboxylic acid, an alcohol, water, sulfur dioxide or a metal oxide such as titanium oxide. Such methods are schematically shown as follows:

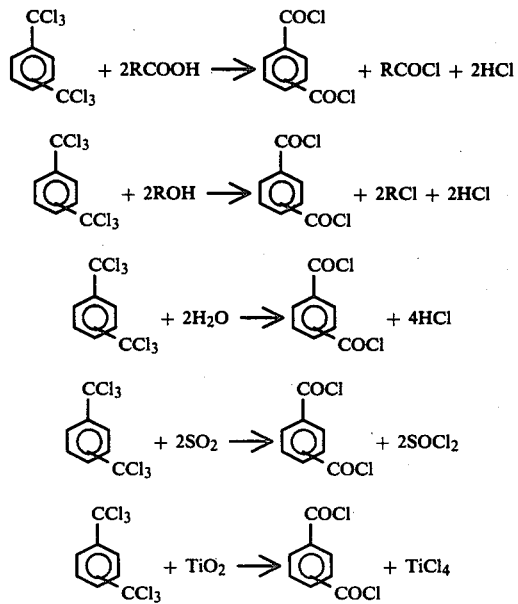

The isophthaloyl dichloride and terephthaloyl dichloride find increasing utility as materials for the production of wholly aromatic polyamides or wholly aromatic polyesters which have recently aroused interest as excellent thermally stable polymers. Since the high purity of isophthaloyl dichloride or terephthaloyl dichloride is of paramount importance in obtaining end polymers of superior properties, it is necessary to produce isophthaloyl dichloride or terephthaloyl dichloride having the highest possible purity.

Generally, a process for preparing isophthaloyl dichloride (abbreviated IPC) or terephthaloyl dichloride (abbreviated TPC) through hexachloroxylene (abbreviated HCX) is economically advantageous. In particular, a method for producing IPC or TPC by reacting HCX with isophthalic acid or terephthalic acid is very advantageous because as shown in formulae (I) and (II), both of the starting xylene and phthalic acid can be converted to phthaloyl dichloride (PC) as an end product. However, in the step of producing HCX by chlorinating the side-chain methyl groups of xylene, by-product impurities, such as a compound resulting from the chlorination of the benzene nucleus and compounds resulting from the decomposition of the ring-chlorinated products, occur inevitably, and it is extremely difficult to remove these impurities. Phthaloyl dichlorides synthesized from HCX containing such impurities contain impurities ascribable to the aforesaid impurities present in HCX. These impurities are also difficult to remove, and at the same time, these impurities cause a marked reduction in the quality of wholly aromatic polyamides or wholly aromatic polyesters prepared from the resulting phthaloyl dichlorides. Accordingly, the removal of impurities is an important problem in the method for producing phthaloyl dichlorides through HCX.

For the production of PC of high purity, the use of HCX having least possible impurities as a starting material of the reaction of equation (II) is thought to be advantageous. This would immediately lead to an idea of purifying the HCX obtained by the reaction of equation (I) by a customary purifying method such as distillation or recrystallization. However, the HCX is extremely difficult to purify, and neither of the distillation method nor the recrystallization method can give satisfactory purities. The fact is that since the boiling points of impurities present in HCX are quite close to that of HCX, distillation is unsatisfactory for separating these impurities from HCX. On the other hand, if HCX is purified by recrystallization, a considerable amount of the end product HCX is lost during purification because HCX has a high solubility in organic solvents and particularly, hexachloro-metaxylene has a low melting point. Thus, the recrystallization method cannot be put to practical use.

For this reason, the purification of PC synthesized through HCX generally does not rely on the purification of HCX obtained by the first step, but on the purification of PC itself from the second step. Distillation is a main method now in use for purifying PC obtained by the second step. A generally employed method for purification of PC consists of distilling the resulting PC after the second step with or without purification of HCX obtained in the first step by distillation. For example, British Pat. No. 946,491 gave consideration to the fact that the purification of HCX by distillation or recrystallization is a difficult and costly operation, and suggested a method of producing isophthaloyl dichloride which comprises distilling the crude isophthaloyl dichloride obtained by the second step, under an absolute pressure of 20 to 50 mmHg, separating a distillate forecut amounting to up to 10% of the crude isophthaloyl dichloride and collecting the balance of the distilled isophthaloyl dichloride as a product having a purity of at least 97% and a melting point of 41° to 43° C. Purification of impurities contained in the crude PC are difficult to remove by distillation because their boiling points are close to that of PC. PC of sufficiently high purity cannot be obtained even if the rates of cutting at the foreward distillation section and the rearward distillation section are increased at a sacrifice of the yield of PC.

Nevertheless, it has been the previous practice to purify PC by distillation, and purification by recrystallization has been considered to be disadvantageous over purification by distillation. The reason for this is that the loss of PC by a recrystallization operation is great, and a satisfactory purity cannot be obtained by only one recrystallization operation, since the amounts of impurities in PC are fairly large and the solubilities of PC and the impurities in organic solvents are similar to each other and also high. Because recrystallization can progressively increase the purity of PC by repeated operations, it is not impossible in principle to obtain PC of the desired high purity if without regard to the yield of PC, the recrystallization is repeated until the desired purity is attained. The repetition of recrystallization, however, is very disadvantageous for commercial operations because it results in a progressive decrease in yield and a markedly high cost of production. Furthermore, since an especially high purity is required of PC as a material for the production of wholly aromatic polyesters or wholly aromatic polyamides, it has previously been thought that recrystallization would be commercially unacceptable for purification of PC as such.

It is an object of this invention to provide a process by which PC of a far higher purity than PC purified by the conventional distillation method can be obtained very economically by a combination of specified manufacturing conditions for obtaining PC through HCX and the recrystallization of the resulting PC under specified conditions.

Another object of this invention is to provide a process which can remove the previous need to choose between purity and yield in the recrystallization of PC produced through HCX.

According to the process of this invention, PC of very high purity can be obtained by only one recrystallizing operation.

SUMMARY OF THE INVENTION

The present invention provides a batchwise or continuous process for producing isophthaloyl dichloride or terephthaloyl dichloride having a high purity which comprises, in combination, (1) a first step of producing $\alpha,\alpha,\alpha,\alpha',\alpha',\alpha'$-hexachloroxylene by reacting a xylene compound selected from the group consisting of (i) xylene selected from meta-xylene and para-xylene and (ii) compounds resulting from the partial chlorination of the side-chain methyl groups of the xylene, with chlorine under the irradiation of ultraviolet-containing rays, the reaction being carried out in the presence of, as a solvent, $\alpha,\alpha,\alpha,\alpha',\alpha',\alpha'$-hexachloroxylene added at the outset of the reaction;

(2) a second step of producing isophthaloyl dichloride or terephthaloyl dichloride by reacting the $\alpha,\alpha,\alpha,\alpha',\alpha',\alpha'$-hexachloroxylene obtained in the first step with isophthalic acid or terephthalic acid; and (3) a third step of purifying the isophthaloyl dichloride or terephthaloyl dichloride obtained in the second step by dissolving the isophthaloyl dichloride or terephthaloyl dichloride in 0.3 to 6 parts by weight, per part by weight of the phthaloyl dichloride, of a $C_6$–$C_{10}$ aliphatic hydrocarbon solvent, and cooling the solution to a temperature within the range of $-20°$ C. to $+20°$ C. in the case of the isophthaloyl dichloride or to a temperature within the range of $-20°$ C. to $+50°$ C. in the case of the terephthaloyl dichloride, thereto to recrystallize the phthaloyl dichloride.

DETAILED DESCRIPTION OF THE INVENTION

Broadly, the invention comprises a first step of producing HCX, a second step of producing PC from HCX, and a third step of purifying the resulting PC. The characteristic feature of the invention is that each step is to be carried out under specified conditions, and only the combination of the three specified steps can achieve the advantage of obtaining PC of high purity economically in very good yields. The first step of the invention is unique in that the chlorination reaction is carried out in the presence of $\alpha,\alpha,\alpha,\alpha',\alpha',\alpha'$-hexachloroxylene (to be referred to as $\alpha,\alpha'$-hexachloroxylene or $\alpha,\alpha'$-HCX for brevity), the final product of this reaction, which is added at the outset of the reaction. In this respect, the first step of this invention differs from the conventional method for producing $\alpha,\alpha'$—HCX. In the second step of the invention, isophthalic acid or terephthalic acid is specifically chosen as a compound to be reacted with HCX to form PC, despite the fact that other various compounds such as monocarboxylic acids, alcohols, water, sulfur dioxide or metal oxides are also available as such a compound. The third step of this invention has an important significance in that recrystallization which has heretofore been considered as less advantageous than distillation for purification of PC is specifically selected as a purifying means, and the recrystallization should be carried out under the special conditions given hereinabove.

The individual steps of the process of this invention are described in greater detail hereinbelow.

The first step of the process of this invention is substantially the same as the process for producing HCX disclosed in U.S. Pat. No. 4,048,033 granted to U.S. patent application No. 504,989 filed on Sept. 10, 1974 by the present applicants. This U.S. Patent is incorporated herein as a reference. The U.S. Patent, however, does not teach that PC synthesized through HCX obtained by the disclosed process can be recrystallized, rather than distilled, to PC of high purity.

The first step of the invention includes both a step of obtaining $\alpha,\alpha'$-hexachloro-m-xylene by chlorinating m-xylene or compounds resulting from the partial chlorination of its side-chain methyl groups to perchlorinate the side-chain methyl groups, and a step of obtaining $\alpha,\alpha'$-hexachloro-p-xylene by chlorinating p-xylene or compounds resulting from the partial chlorination of its side-chain methyl groups to perchlorinate the side-chain methyl groups. The compounds resulting from the partial chlorination of the side-chain methyl groups of xylene denote compounds resulting from the partial chlorination of at least one side-chain methyl group, and include, for example, $\alpha$-chloro-m-xylene, $\alpha,\alpha'$-dichloro-m-xylene, $\alpha$-chloro-p-xylene, or $\alpha,\alpha'$-dichloro-p-xylene.

The $\alpha,\alpha'$-hexachloroxylene to be present in the reaction system as a solvent from the outset of the reaction in the first step is $\alpha,\alpha'$-hexachloro-m-xylene when the intended product is $\alpha,\alpha'$-hexachloro-m-xylene, and is α,α'-hexachloro-p-xylene when the intended product is α,α'-hexachloro-p-xylene.

The chlorination reaction in the first step of the invention can be performed either batchwise or continuously.

The amount of the hexachloroxylene added as a solvent in the first step differs between the batchwise method and the continuous method. In the case of the batchwise method, the solvent is added in an amount of 0.3 to 15 parts by weight, preferably 0.8 to 5 parts by weight, per part by weight of the starting xylene or a compound resulting from the partial chlorination of its side-chain methyl groups, and then the reaction is started. In the case of the continuous method, the reaction is carried out while continuously feeding the material with the concentration of the hexachloroxylene in the reaction mixture within the reactor being adjusted to 40 to 99% by weight, preferably 70 to 99% by weight.

In the first step of the process of this invention, the reaction temperature is 80° to 160° C., preferably 100° to 150° C., in the case of reacting m-xylene or a compound resulting from the partial chlorination of its methyl groups, and 110° to 160° C., preferably 120° to 150° C., in the case of reacting p-xylene or a compound resulting from the partial chlorination of its methyl groups.

The amount of chlorine may be in a large excess in the case of the batchwise method, and the sufficient amount is 110 to 160% of the stoichiometrical amount. In the case of the continuous method, it is not altogether necessary to add it in excess. In feeding chlorine, it is desirably dispersed as the finest possible bubbles in the reaction mixture.

The second step of this invention is directed to the production of phthaloyl dichlorides by reacting the α,α'-hexachloroxylene obtained in the first step with the corresponding phthalic acid. Isophthaloyl dichloride can be obtained by the reaction of equation (II) in which the α,α'-hexachloro-m-xylene is reacted with isophthalic acid. The reaction of the α,α'-hexachloro-p-xylene with terephthalic acid yields terephthaloyl dichloride.

If desired, the reaction product obtained in the first step can be purified by such an operation as distillation or recrystallization prior to its reaction with isophthalic acid or terephthalic acid. Without such a purification procedure, the process of this invention can afford PC of a very high purity, and from the viewpoint of yield, it is desirable to omit such a purification step. This is also among the advantages of this invention.

In the second step, the hexachloroxylene is used desirably in an amount nearly equimolar to the amount of the phthalic acid. If the amount of the hexachloroxylene is in too large an excess to the phthalic acid, the yield of the final product decreases because the hexachloroxylene remains or a compound having a trichloromethyl group is newly formed. On the other hand, if the amount of the phthalic acid is in too large an excess with regard to the hexachloroxylene, a condensation product between the resulting phthaloyl dichloride and the excess of the phthalic acid forms and remains, so that the yield of the final product decreases. Hence, the crude hexachloroxylene is used in an amount, calculated as pure hexachloroxylene, of 0.90 to 1.10 moles, preferably 0.95 to 1.05 moles, per mole of the phthalic acid.

In the second step, a Friedel-Crafts catalyst, such as aluminum chloride, antimony chloride, ferric chloride, titanium tetrachloride, tin tetrachloride and zinc chloride, is used. Ferric chloride is an especially preferred catalyst. The amount of the catalyst is 0.01 to 0.5% by weight based on the mixture of hexachloroxylene and phthalic acid.

The reaction temperature in the second step is 50° to 150° C. in the case of producing isophthaloyl dichloride, and 120° to 180° C. in the case of producing terephthaloyl dichloride.

The reaction in the second step is continued until insoluble substances such as the phthalic acid vanish and there is scarcely any evolution of hydrogen chloride.

The third step of the present invention involves the purification by recrystallization of the crude PC obtained by the second step. The reaction mixture obtained by the second step also contains the catalyst or tarry by-products as impurities. Since these impurities cause the reduction of yield in the recrystallization step and reduces the purity of the final product, it is preferred to remove the catalyst and the tarry substances by distilling the reaction mixture from the second step before submitting it to recrystallization.

In performing the purification by a recrystallization method in the third step, it is necessary to use a solvent which does not react with phthaloyl dichlorides and has a solubility suitable for recrystallization, because the phthaloyl dichlorides are very reactive.

The freezing point of isophthaloyl dichloride is about 43° C., and that of terephthalic dichloride, about 81° C. Thus, these compounds, especially the isophthaloyl dichloride having a low freezing point, are extremely difficult to purify by a recrystallization method. As a result of various investigations about the ecrystallization of phthaloyl dichlorides, the present inventors found that phthaloyl dichlorides of high purity can be obtained by performing the crystallization under the conditions to be described hereinbelow.

Aliphatic hydrocarbons containing 6 to 10 carbon atoms are suitable solvents for use in the recrystallization of the phthaloyl dichloride in the third step. Specific examples include n-hexane, methylcyclopentane, 2-methylpentane, 2,2-dimethylbutane, 3-methylpentane, cyclohexane, n-heptane, 2-methylhexane, methylcyclohexane, 3-methylhexane, 2,2-dimethylpentane, n-octane, 2,2,3,3-tetramethylbutane, 2,2,4-trimethylpentane, 2-methylheptane, n-nonane, 2-methyloctane, 2,4-dimethylheptane, 2,5-dimethylheptane, n-decane, 2-methylnonane, 2,6-dimethyloctane, and 2,7-dimethyloctane. Of these, hexanes, especially n-hexane, are preferred.

These aliphatic hydrocarbon are used singly or as mixtures of two or more. If desired, a mixture of at least 95% by weight of the $C_6$–$C_{10}$ aliphatic hydrocarbon and up to 5% by weight of an aliphatic hydrocarbon containing up to 5 carbon atoms or at least 11 carbon atoms or an aromatic hydrocarbon may be used.

The amount of the solvent used is generally 0.3 to 6.0 parts by weight, preferably 0.4 to 4.0 parts by weight, per part by weight of terephthaloyl dichloride. If the amount of the solvent is less than 0.3 part by weight, the separation of impurities becomes difficult, and the impurities are sometimes included in the phthaloyl dichloride. On the other hand, if the amount of the solvent is larger than 6.0 parts by weight, the recovery ratio of the phthaloyl dichloride decreases. Hence, amounts outside the specified ranges are not preferred.

The temperature to which the aliphatic hydrocarbon solution of the phthaloyl dichloride is cooled for crystallization is generally −20° C. to +20° C., preferably −10° C. to +15° C., in the case of the isophthaloyl dichloride. In the case of terephthaloyl dichloride, the cooling temperature is generally −20° C. to +50° C., preferably −5° C. to +30° C. If the cooling temperature is below −20° C. which is the lower limit, the energy is wasted in cooling the solution. If the cooling temperature is higher than the upper limit (that is, +20° C. for IPC and +50° C. for TPC), the phthaloyl dichloride frequently remains in the solvent. Hence, cooling temperatures outside the specified range are not preferred.

Desirably, the third step of the process of this invention should be performed, to the greatest possible extent, in the absence of moisture because if the recrystallization solvent contains water or the phthaloyl dichloride contacts the outer atmosphere having a high humidity, the phthaloyl dichloride undergoes partial hydrolysis to phthalic acid to reduce the yield of the final compound and at the same time, hydrogen chloride formed by the hydrolysis exerts various undesirable effects.

The phthaloyl dichloride as purified by the recrystallization in the third step has such a quality as can be useful in various applications. If a higher quality is desired, it is then distilled to remove impurities resulting from the recyrstallization operation in the third step which include the recrystallization solvent and traces of free phthalic acids, etc.

The phthaloyl dichlorides produced by the process of this invention are of extremely high purity, and have very good suitability as materials for the production of thermally stably wholly aromatic polyamides or polyesters. In the process for this invention, it is essential that in the production of HCX by chlorination in the first step. HCX should be caused to be present from the outset of the reaction. The important significance of the invention lies in the fact that it permits a reevaluation of the recrystallization method heretofore considered commercially infeasible for purification of PC as a result of combining the first step under such special reaction conditions with the recrystallization conditions in the third step. In principle, recrystallization is advantageous over distillation since it can remove impurities having boiling points close to that of PC which cannot be removed by distillation. Despite this fact, the recrystallization method has not come into commercial acceptance because of the need to choose between purity and yield. The present invention has obviated the need for such a choice, and makes it possible to utilize fully the inherent advantages of the recrystallization method.

As stated hereinabove, the applicants suggested a process for preparing $\alpha,\alpha'$-hexachloroxylene of high purity in U.S. Pat. 4,048,033. It was found that HCX produced by this process contains small amounts of impurities which are still difficult to separate, and if PC is produced from HCX and a thermally stable polymer is produced from PC, the inclusion of the above impurities, even in small amounts, adversely affects the properties of the final thermally stable polymer. In an attempt to remedy this defect, the applicants proposed in U.S. Pat. No. 4,029,560 granted to U.S. patent application Ser. No. 671,698 filed Mar. 16, 1976 an improved process which comprises preparing $\alpha,\alpha'$-hexachloroxylene in a first step, and subsequently subjecting the product to post-chlorination reaction in a second step to convert impurities which are difficult to separate by distillation into compounds which are easy to separate by distillation. The applicants disclosed in the specification of U.S. Pat. No. 4,029,560 that if the $\alpha,\alpha'$-hexachloroxylene obtained by the process of U.S. Pat. No. 4,029,560 is reacted with phthalic acid and the resulting PC is then purified by distillation, the purity of PC is considerably increased, and the properties of a thermally stable polymer prepared from PC are also considerably improved. However, as shown in Examples to be given hereinbelow, it has been found that PC obtained by the process of this invention has a higher purity than PC obtained by the process of U.S. Pat. No. 4,029,560, and the properties of thermally stable polymers produced from the resulting PC are better in the present invention than in U.S. Pat. No. 4,029,560. In addition, since the yield of PC is far higher in the present invention than in U.S. Pat. No. 4,029,560, the process of this invention is far superior to that in U.S. Pat. No. 4,029,560.

An additional advantage is that the process of this invention can permit a reduction in the cost of equipment and the cost of chemicals (chlorine) because it does not require the second-stage post chlorination which is essential in U.S. Pat. No. 4,029,560.

It is surprising that when the PC obtained by the process of U.S. Pat. No. 4,029,560 is subjected to the recrystallization operation of the third step of this invention, the resulting PC has a purity substantially equivalent to that of the PC obtained by the process of this invention. The process of U.S. Pat. No. 4,029,560 brings about an increase in the purity of PC as a result of attaching a post-chlorination step to the process of U.S. Pat. No. 4,048,033. Hence, if this PC having an increased purity is subjected to the recrystallization operation in the third step of this invention, a higher purity of PC would be expected to be achieved than when the PC obtained by the second step of the invention is subjected to the recrystallization operation of the third step of the invention. In fact, the result is that the purities of the purified PC in these two methods are substantially the same. This is quite an unexpected result, which suggests that the purity of PC obtained by the process of this invention has been increased nearly to the highest point that can be achieved.

The following Examples and Comparative Examples illustrate the process of this invention. Since the freezing point of PC is a very good measure for the purity of PC, the purities of PC in the following examples are shown by their freezing points measured by the method of JIS K-4101.

EXAMPLE 1

(A) A 2-liter flask equipped with a thermometer, a chlorine introducing tube, a reflux condenser concurrently acting as a gas exhaust means and a double cooling tube for cooling a light source was charged with 400 g. (3.77 moles) of m-xylene and 800 g of $\alpha,\alpha'$-hexachloro-m-xylene. The contents were heated to 130° C., and while irradiating light by a 100 W internally irradiating high pressure mercury lamp, chlorine was blown into the flask with stirring by an electromagnetically operated stirrer. The introduction of chlorine was performed at a rate of about 3.8 moles/hour for the first 5 hours. Then, the amount of chlorine introduced was somewhat decreased, and the reaction was performed for an additional 3 hours. The total amount of chlorine which was introduced up to this time was 118% of the amount stoichiometrically required to synthesize α,α'-hexachloro-m-xylene from m-xylene. After the reaction, chlorine and hydrogen chloride gases in the flask were removed by passing dry nitrogen gas. The reaction mixture was obtained in an amount of 1969 g. The yield of the crude α,α'-dexachloro-m-xylene calculated from an increase in the amount of the reaction mixture was 99.1% based on m-xylene. A gas-chromatographic analysis of this product showed that the concentration of α,α'-hexachloro-m-xylene was 98.5% by weight. If it is supposed that α,α'-hexachloro-m-xylene obtained by removing 800 g of α,α'-hexachloro-m-xylene initially added was newly formed, the yield of the α,α'-hexachloro-m-xylene based on m-xylene is 96.6%.

(B) A mixture of 313 g (corresponding to about 1 mole, because the molecular weight of α,α'-hexachloro-m-xylene is 313) of the crude α,α'-hexachloro-m-xylene obtained in (A) above, 166 g (1.00 mole) of isophthalic acid and 0.48 g of anhydrous ferric chloride was heated with stirring. At about 60° C., hydrogen chloride began to be evolved. The reaction was performed for about 40 minutes at this temperature. Then, the temperature was raised to 100° C. over the course of about 30 minutes, and the reaction was further carried out for 20 minutes at 100° C. to terminate it. The crude product obtained was subjected to simple distillation at 118° to 121° C. under a pressure of 3 to 5 mmHg to remove distillable substances as much as possible. Thus, 398 g of crude isophthaloyl dichloride was obtained. The yield of the crude isophthaloyl dichloride was 98.0%.

(C) The crude isophthaloyl dichloride obtained in (B) was mixed with 0.6 part by weight, per part by weight, of n-hexane, and heated. The solution was cooled to −5° C. to crystallize isophthaloyl dichloride sufficiently. The crystals were separated from the mother liquor, and quickly washed with 0.2 part by weight, per part by weight of the crude isophthaloyl dichloride, of cold n-hexane. The crystalline isophthaloyl dichloride obtained was subjected to simple distillation at 118° to 121° C. under a pressure of 3 to 5 mmHg to obtain purified isophthaloyl dichloride in a recovery ratio of 93% based on the crude isophthaloyl dichloride. The purified product had a freezing point of 43.80° C. The total yield of the purified isophthaloyl dichloride based on the starting m-xylene was 90.3%.

EXAMPLE 2

(A) The same chlorinating reactor as used in Example 1 was charged with 400 g (3.77 moles) of m-xylene and 800 g of the crude reaction mixture obtained in Example 1, (A), and the reaction was performed by the same operation as in Example 1. After the reaction, chlorine and hydrogen chloride dissolved in the reaction mixture were driven off by passing dry nitrogen gas. Thus, 1966 g of the reaction mixture was obtained. The yield of the crude α,α'-hexachloro-m-xylene, calculated from an increase in the amount of the reaction mixture from the amount initially charged, was 98.9% based on m-xylene. A gas-chromatographic analysis of this product showed that the concentration of α,α'-hexachloro-m-xylene was 98.0% by weight. The amount of α,α'-hexachloro-m-xylene in the reaction mixture was found to be 1926.7 g. If it is supposed that α,α'-hexachloro-m-xylene obtained by removing the α,α'-hexachloro-m-xylene initially present in the crude reaction mixture added was newly formed, the yield of this product based on the starting m-xylene is 96.5%.

(B) A mixture of 313 g (about 1 mole) of the crude α,α'-hexachloro-m-xylene obtained in (A), 166 g (1.00 mole) of isophthalic acid and 0.48 g of anhydrous ferric chloride was heated with stirring, and reacted in the same way as in Example 1, (B).

The crude product so obtained was subjected to simple distillation in the same way as in Example 1, (B) to afford 397 g of crude isophthaloyl dichloride. The yield of the crude isophthaloyl dichloride based on isophthalic acid was 97.8%.

(C) The crude isophthaloyl dichloride obtained in (B) above was recrystallized by the same procedure as in Example 1, (C), and then subjected to simple distillation to afford purified isophthaloyl dichloride in a recovery ratio of 93% based on the crude isophthaloyl dichloride. The purified product has a freezing point of 43.80° C. The total yield of the purified isophthaloyl dichloride based on the starting m-xylene was 90.0%.

COMPARATIVE EXAMPLE 1

This example shows an experiment in which chlorination in the first step was performed in the absence of α,α'-hexachloro-m-xylene as a solvent.

(A) m-Xylene (680 g; 6.40 moles) was taken into the same chlorinating reactor as used in Example 1, and heated to 130° C. While irradiating light by a 100 W internally irradiating high pressure mercury lamp, chlorine gas was blown into the reactor with stirring. The amount of chlorine introduced was about 6.4 moles/hour for the first 5 hours. Then, the amount of chlorine blown was somewhat decreased, and the reaction was carried out for an additional 3 hours. After the reaction, dry nitrogen gas was passed to remove chlorine and hydrogen chloride dissolved in the reaction system. Thus, 1966 g of the reaction mixture was obtained. The yield of the crude α,α'-hexachloro-m-xylene calculated from an increase in the amount of the reaction mixture was 98.2% based on the m-xylene. A gas-chromatographic analysis of this product showed that the concentration of α,α'-hexachloro-m-xylene was 90.6% by weight. Analysis showed that the amount of the resulting α,α'-hexachloro-m-xylene was 1781 g, and its yield based on m-xylene was 89.0%.

(B) A mixture of 313 g (about 1 mole) of the crude α,α'-hexachloro-m-xylene obtained in (A), 166 g (1.00 mole) of isophthalic acid, and 0.48 g of anhydrous ferric chloride was heated with stirring, and reacted in the same way as in Example 1, (B).

The crude product obtained was subjected to short-path distillation in the same way as in Example 1, (B) to afford 383 g of crude isophthaloyl dichloride. The yield of the crude isophthaloyl dichloride based on the crude α,α'-hexachloro-m-xylene charged was 94.3%.

(C) The crude isophthaloyl dichloride obtained in (B) was mixed with 0.6 part by weight, per part by weight of the isophthaloyl dichloride, of n-hexane. The mixture was subjected to recrystallization and short-path distillation by the same procedure as in Example 1, (C) to afford purified isophthaloyl dichloride in a recovery ratio of 91% based on the crude isophthaloyl dichloride. The purified product had a freezing point of 43.68° C. The total yield of the purified isophthaloyl dichloride was 84.3% based on the starting m-xylene.

(D) The crude isophthaloyl dichloride was recrystallied and then subjected to simple distillation by the same procedure as in (C) above except that the amount of n-hexane used was changed to 0.5 part by weight per part by weight of the crude phthaloyl dichloride. Thus, purified isophthaloyl dichloride was obtained in a recovery ratio of 93% based on the crude isophthaloyl dichloride. The purified product had a freezing point of 43.42° C. The total yield of the purified isophthaloyl dichloride based on the starting m-xylene was 92.7%.

COMPARATIVE EXAMPLE 2

(A) The crude α,α'-hexachloro-m-xylene obtained in Comparative Example 1, (A) was distilled at 154° to 158° C. under a pressure of 10 mmHg using an about 60 cm-long column packed with porcelain Rasching rings. The first and last fractions were cut, and the remainder of the distillate was recovered in a recovery ratio of 75% based on the α,α'-hexachloro-m-xylene charged. The recovered distillate was found to have a purity of 99.3% as a result of its gas-chromatographic analysis.

(B) A mixture of 313 g of the purified α,α'-hexachloro-m-xylene obtained in (A), 166 g of isophthalic acid and 0.48 g of anhydrous ferric chloride was reacted in the same way as in Example 1, (B). After the reaction, the crude product was distilled at 118° and 121° C. under a pressure of 3 to 5 mmHg using an about 20 cm-long Vigreaux column to afford 394 g of isophthaloyl dichloride. The yield of the product based on the α,α'-hexachloro-m-xylene was 97.0%. The product had a freezing point of 43.38° C.

The total yield of the purified isophthaloyl dichloride based on the starting m-xylene was 71.4%.

EXAMPLE 3

(A) A 2-liter glass reactor equipped with an internally irradiating high pressure mercury lamp with a double cooling tube, same as that used in Example 1, was charged with 425 g (4.00 moles) of p-xylene and 700 g of α,α'-hexachloro-p-xylene. The contents were heated to 135° C., and while irradiating light by a 100 W high pressure mercury lamp, chlorine was blown into the reactor with stirring. The amount of chlorine introduced was about 4.0 moles/hour for the first 5 hours. Then, the rate of introducing chlorine was somewhat decreased, and the reaction was performed for an additional 3 hours. The amount of chlorine which had been blown into the reactor up to this time was 120% of the amount stoichiometrically required to synthesize α,α'-hexachloro-p-xylene from p-xylene. After the reaction, dry nitrogen gas was passed through the reactor to remove chlorine and hydrogen chloride gas in the reaction system. Thus, 1930 g of the reaction mixture was obtained. A gas-chromatographic analysis of the reaction mixture showed that the concentration of α,α'-hexachloro-p-xylene was 98.3% by weight. If it is supposed that the newly formed reaction mixture is the one obtained by removing the initially charged mixture from the finally obtained reaction mixture, the yield of the crude α,α'-hexachloro-p-xylene based on p-xylene is 98.3%.

(B) A mixture of 313 g (about 1 mole) of the crude α,α'-hexachloro-p-xylene obtained in (A), 168 g (1.01 moles) of terephthalic acid and 0.38 g of anhydrous ferric chloride was heated, and with stirring, reacted at 130° C. for 30 minutes. The temperature was then raised to 150° C. over the course of about 30 minutes, and the reaction was further performed at this temperature for 20 minutes to terminate it. After the reaction, the crude product was subjected to simple distillation at 117° to 121° C. under a pressure of 3 to 5 mmHg to remove all distillable materials. Thus, 391 g of crude terephthaloyl dichloride was obtained. The yield of the crude terephthaloyl dichloride based on the crude α,α'-hexachloro-p-xylene was 96.3%.

(C) The crude terephthaloyl dichloride obtained in (B) was mixed with 1 part by weight, per part by weight of the crude terephthaloyl dichloride, of octane and heated. The solution was subjected to recrystallization at a crystallizing temperature of 0° C. The crystalline portion left after the separation of the mother liquor was washed with 0.3 part by weight of cold octane. The crystalline terephthaloyl dichloride so obtained was subjected to simple distillation at 117° to 121° C. under a pressure of 3 to 5 mmHg. Purified terephthaloyl dichloride was thus obtained in a recovery ratio of 93% based on the crude terephthaloyl dichloride. The purified product had a freezing point of 81.72° C.

The total yield of the purified terephthaloyl dichloride based on the starting p-xylene was 88.0%.

COMPARATIVE EXAMPLE 3

(A) The same reactor as used in Example 3, (A) was charged with 400 g (3.77 moles) of p-xylene and 800 g of carbon tetrachloride. The contents were heated to 75° C., and under the irradiation of light, chlorine gas was blown into the reactor to perform the reaction. The amount of chlorine introduced was 3 moles/hour for the first 6 hours. Then, the amount of chlorine was somewhat decreased, and the reaction was performed for an additional 4 hours. After the reaction, the solvent was evaporated off to afford 1168 g of the reaction mixture. The yield of the crude, α,α'-hexachloro-p-xylene calculated from an increase in the amount of the reaction mixture was 99.0% based on p-xylene. A gas-chromatographic analysis of this reaction mixture showed that the concentration of α,α'-hexachloro-p-xylene was 93.9% by weight. The resulting crude α,α'-hexachloro-p-xylene was distilled at 158° to 162° C. under a pressure of 10 mmHg using an about 60 cm-long column packed with porcelain Raschig rings. The first and last fractions were cut, and the main fraction was obtained in a ratio of about 80% based on the amount of the material initially charged. The main fraction was found to have a purity of 99.3% as a result of its gas-chromatographic analysis.

(B) A mixture of 313 g of the purified α,α'-hexachloro-p-xylene, 168 g of terephthalic acid and 0.38 g of anhydrous ferric chloride was reacted in the same way as in Example 3, (B). After the reaction, the crude reaction product was distilled at 117° to 121° C. under a pressure of 3 to 5 mmHg using an about 20 cm-long Vigreaux column to afford 390 g of terephthaloyl dichloride having a freezing point of 81.30° C.

The total yield of the purified terephthaloyl dichloride based on the starting p-xylene was 76.0%.

EXAMPLE 4

(A) A 2-liter glass flask equipped with a light irradiating device, a thermometer, a stirrer, a reflux condenser, a chlorine introducing inlet, an m-xylene feed opening and an opening for overflowing the reaction mixture was filled with α,α'-hexachloro-m-xylene up to the vicinity of the overflowing opening. The contents were heated to 135° C. Under the irradiation of light, m-xylene was fed continuously at a rate of about 81 g/hour (0.76 mole/hour) and chlorine, at a rate of about 390 g/hour (5.50 moles/hour). The m-xylene had been preheated to 120° to 130° C. prior to feeding to the reactor. Chlorine was bubbled in gas form at the bottom of the reactor. The gas exhausted from the reactor was fully cooled through the condenser, and let out of the reaction system from the top of the condenser. The reaction mixture which increased as a result of the feeding of m-xylene and the reaction overflowed from the overflowing opening, and removed out of the reaction system. In this example, the volume of that portion of the reactor which was filled with the liquid was about 1.8 liters.

The reaction was performed under these conditions for 40 hours. The reaction mixture was then analyzed by gas chromatography. It was found that the concentration of $\alpha,\alpha'$-hexachloro-m-xylene was 95.2% by weight.

In the same manner, the reaction was carried out for an additional 20 hours. During this time, 1616 g (15.22 moles) of m-xylene and 7808 g (110.11 moles) of chlorine were fed, and 4720 g of the reaction mixture was obtained. The yield of the crude, $\alpha,\alpha'$-hexachloro-m-xylene calculated from an increase in the amount of the reaction mixture was 99.1% based on m-xylene. A gas-chromatographic analysis of the reaction mixture showed that it consisted of 95.6% by weight of $\alpha,\alpha'$-hexachloro-m-xylene, 0.8% by weight of chlorinated intermediates obtained in the route from m-xylene to $\alpha,\alpha'$-hexachloro-m-xylene, and 4.0% by weight of other compounds. The results of analysis show that 4512 g of $\alpha,\alpha'$-hexachloro-m-xylene was formed during the 20-hour period which ran from 40 hours to 60 hours after the reaction.

The yield of the product based on the starting m-xylene was 94.8% by weight.

(B) A mixture of 313 g (1.00 mole) of the crude $\alpha,\alpha'$-hexachloro-m-xylene obtained in (A) above, 168 g (1.01 moles) of isophthalic acid and 0.38 g of anhydrous ferric chloride was heated with cooling. At about 60° C., the reaction began with the evolution of gases. The reaction was performed at this temperature for 30 minutes. The temperature of the solution was then raised to 130° C. over the course of 30 minutes. The reaction was carried out at 130° C. for an additional 20 minutes to terminate it. The crude reaction product was subjected to simple distillation at 118° C. to 121° C. under a pressure of 3 to 5 mmHg to afford 395 g of crude isophthaloyl dichloride. The yield of the crude isophthaloyl dichloride based on the crude $\alpha,\alpha'$-hexachloro-m-xylene was 97.3%.

(C) The crude isophthaloyl dichloride obtained in (B) was recrystallized and subjected to simple distillation in the same way as in Example 1, (C) to afford purified isothphthaloyl dichloride in a recovery ratio of 93% based on the crude isophthaloyl dichloride.

The total yield of the purified isophthaloyl dichloride based on the starting m-xylene was 89.7%.

EXAMPLE 5

(A) A 2-liter glass reactor equipped with an internally irradiating high pressure mercury lamp device with a double cooling tube was used as a main reactor, and a 500 ml glass reactor equipped with an internally irradiating high pressure mercury lamp device with a double cooling tube was used as a rearward reactor. The main reactor was positioned at a higher level than the rearward reactor, and the reaction mixture-overflowing opening of the main reactor was connected to the reaction mixture-feed opening of the rearward reactor. The volume of the reactor up to the overflowing opening was 1.8 liters in the main reactor, and 400 ml in the rearward reactor.

Each of the reactor was filled with $\alpha,\alpha'$-hexachloro-p-xylene, and the temperature of the liquid was raised to 130° C. When the temperature of the liquid reached 130° C., p-xylene and chlorine were continuously fed under the irradiation of light to perform the reaction.

The rate of p-xylene fed to the main reactor was about 81 g/hour (0.763 mole/hour). The amounts of chlorine fed as 390 g/hour (5.50 moles/hour) in the main reactor, and 40 g/hour (0.56 mole/hour) in the rearward reactor.

The reaction was performed under the above conditions. During the 20-hour period from 40 hours to 60 hours after the start of the reaction, 1626 g (15.32 moles) of p-xylene was fed into the main reactor, and the chlorine was fed in an amount of 7796 g (109.9 moles) into the main reactor, and in an amount of 795 g (11.2 moles) into the rearward reactor. After the reaction, chlorine and hydrogen chloride dissolved were removed by passing dry nitrogen gas. Thus, 4756 g of the reaction mixture was obtained. The yield of the crude $\alpha,\alpha'$-hexachloro-p-xylene calculated from an increase in the amount of the reaction mixture was 99.2% based on the p-xylene. A gas-chromatographic analysis of the reaction mixture showed that the concentration of $\alpha,\alpha'$-hexachloro-p-xylene was 97.2% by weight. The results of analysis showed that during the 20-hour period from 40 to 60 hours after the start of the reaction, 4623 g of $\alpha,\alpha'$-hexachloro-p-xylene was formed.

The yield of the product based on the starting p-xylene was 96.5%.

(B) A mixture of 313 g (1.00 mole) of the crude $\alpha,\alpha'$-hexachloro-p-xylene obtained in (A) above, 166 g (1.00 mole) of terephthalic acid and 0.48 g of anhydrous ferric chloride was reacted in the same way as in Example 3, (B). After the reaction, the crude reaction product was subjected to simple distillation at 117° C. to 121° C. under a pressure of 3 to 5 mmHg to afford 394 g of crude terephthaloyl dichloride.

The yield of the crude terephthaloyl dichloride based on the crude $\alpha,\alpha'$-hexachloro-p-xylene was 97.0%.

(C) The crude terephthaloyl dichloride obtained in (B) above was mixed with 1 part by weight, per part by weight of the crude terephthaloyl dichloride, of n-hexane, and heated. The solution was subjected to recrystallization at a crystallizing temperature of 10° C. The crystalline portion left after the separation of the mother liquor was washed with 0.4 part by weight of cold n-hexane. The terephthaloyl dichloride obtained was subjected to simple distillation at 117° C. to 121° C. under a pressure of 3 to 5 mmHg to afford purified terephthaloyl dichloride in a recovery ratio of 93% based on the crude terephthaloyl dichloride. The purified product had a freezing point of 81.72° C.

The total yield of the purified terephthaloyl dichloride based on the starting p-xylene was 89.5%.

COMPARATIVE EXAMPLE 4

This example shows an experiment in which hexachloro-m-xylene was produced by performing the second-stage post chlorination disclosed in U.S. Pat. No. 4,029,560 instead of the first step of this invention.

(A) A 2-liter flask equipped with a thermometer, a chlorine introducing tube and a reflux condenser concurrently acting as a gas exhaust means was charged with 400 g (3.77 moles) of m-xylene and 800 g of $\alpha,\alpha'$-hexachloro-m-xylene. The contents were heated to 130° C. While irradiating light by a 100 W internally irradiating high pressure mercury lamp, chlorine gas was blown into the reactor with stirring by an electromagnetically operated stirrer. The amount of chlorine introduced was set at about 269.8 g/hour (3.8 moles/hour) for the first 5 hours. Then, the amount of chlorine introduced was somewhat decreased, and the reaction was carried out for an additional 3 hours. The amount of chlorine used up to this time was 116% of the amount stoichiomerrically required to synthesize α,α'-hexachloro-m-xylene from m-xylene. A gas-chromatographic analysis of the reaction mixture sampled at this point showed that it scarcely contained reaction intermediates which could be converted to α,α'-hexachloro-m-xylene by further chlorination. At this point, the amount of chlorine introduced was changed to 30 g/hour (0.42 mole/hour), and under the irradiation of light, the reaction was performed at 130° C. for 1 hour. After the reaction, dry nitrogen gas was passed through the reactor to remove chlorine and hydrogen chloride gas dissolved in the reaction system. Thus, 1973 g of the reaction mixture was obtained. A gas-chromatographic analysis of this reaction mixture showed that the concentration of α,α'-hexachloro-m-xylene was 98.6% by weight.

If it is supposed that the balance of α,α'-hexachloro-m-xylene obtained by removing 800 g of the α,α'-hexachloro-m-xylene initially charged was the product newly formed, the yield of the α,α'-hexachloro-m-xylene based on m-xylene is 97.1%.

The resulting crude α,α'-hexachloro xylene was distilled under reduced pressure using an about 60 cm-long column packed with porcelain Raschig rings. The first and last fractions were cut, and a fraction boiling at 154°–158° C./10 mmHg was collected in a ratio of about 85% based on the amount initially charged. A gas-chromatographic analysis of this fraction showed that the purity of the α,α'-hexachloro-m-xylene was more than 99.8%.

(B) A mixture of 313 g (1.00 mole) of the purified α,α'-hexachloro-m-xylene obtained in (A) above, 168 g (1.01 moles) of isophthalic acid and 0.48 g of anhydrous ferric chloride was heated with stirring. At about 60° C., hydrogen chloride began to be evolved. The reaction was performed at this temperature for about 40 minutes. Then, the reaction temperature was raised to 100° C. over the course of about 30 minutes, and the reaction was performed at 100° C. for an additional 20 minutes to terminate it. The crude reaction product was distilled at 118° C. to 121° C. under a pressure of 5 mmHg using an about 20 cm-long Vigreaux column to afford 386 g of isophthaloyl dichloride. The resulting isophthaloyl dichloride was mixed with 0.6 part by weight, per part by weight of the crude isophthaloyl dichloride, of n-hexane, and heated. The solution was cooled to −5° C. to crystallize isophthaloyl dichloride sufficiently. The crystals were separated, and quickly washed with 0.2 part by weight, per part by weight of the isophthaloyl dichloride, of cold n-hexane. The resulting crystalline isophthaloyl dichloride was subjected to simple distillation at 118° C. to 121° C. under a pressure of 3 to 5 mmHg to afford purified isophthaloyl dichloride having a freezing point of 43.80° C.

EXAMPLE 6

The phthaloyl dichlorides obtained in the above examples were each reacted with aromatic diamines under given standard polymerization conditions to produce aromatic polyamides. The degrees of polymerization (expressed by viscosities) of the resulting aromatic polyamides were measured. Using the degrees of polymerization as criteria, the suitability of the phthaloyl dichlorides as raw materials for the production of polymers was evaluated.

The standard polymerization conditions and the method for viscosity measurement differed somewhat between isophthaloyl dichloride and terephthaloyl dichloride. The test methods and the results of experiments are given below.

(A) ISOPHTHALOYL DICHLORIDE

Test Method

In a 300 ml well-dried three-necked flask, 12.98 g (0.1200 mole) of m-phenylene diamine was placed, and dissolved in N-methylpyrrolidone with a water content of about 0.01% to form a uniform solution. The solution was cooled to −20° C., and 24.38 g (0.1201 mole) of isophthaloyl dichloride to be tested was added to the solution while stirring it at a speed of about 200 rpm. The temperature of the contents of the flask rose abruptly with the addition of the isophthaloyl dichloride. The addition was completed within 5 minutes while controlling the temperature of the contents of the flask so that it did not exceed 40° C. The resulting non-transparent viscous solution was heated at 40° C. for about 3 hours with stirring, and then added to 2 liters of cold water, followed by stirring for about 15 minutes. The precipitated polymer was filtered, washed with 2 liters of warm water at about 60° C., and dried.

The resulting polymer was dissolved in 95% by weight sulfuric acid, and its relative viscosity ($n_{rel}$) was measured by a viscometer at 25° C. in a concentration of 1 g/100 ml $H_2SO_4$.

$$\eta_{rel} = \frac{\text{Falling time in seconds of the sample solution}}{\text{Falling time in seconds of the 95\% sulfuric acid}}$$

In order that the resulting polymer will have good stretchability and spinnability, it should desirably have as high a relative viscosity as possible.

(B) TEREPHTHALOYL DICHLORIDE

Test Method

A four-necked flask equipped with a nitrogen introducing inlet, a stirring rod and a thermometer was heated by a burner in a stream of nitrogen to remove water adhering to it. 135 ml of N-methylpyrrolidone which had been purified and dried to a substantially anhydrous condition, 65 ml of hexamethyl phosphoric triamide and 3.2453 g (0.0300 mole) of p-phenylenediamine, were precisely weighed, and charged into the flask. A uniform solution was prepared, and the contents of the flask were cooled to 5° C. with an ice bath. Then 6.0927 g (0.0300 mole) of precisely weighed solid terephthaloyl dichloride to be tested was added at a time. When the rise of the temperature of the contents became 20° C., the ice bath was removed, and the reactions mixture was stirred continuously. When the stirring was continued for about 10 minutes, the reaction misture became abruptly viscous, and then changed to a jelly-like mass. The stirring was stopped, and the jelly-like mass was allowed to stand for about 18 hours.

The resulting jelly-like mass was vigorously stirred in a mixer, pulverized, well washed, and filtered to form a polymer powder. The resulting polymer was thoroughly dried, and dissolved in conc. sulfuric acid (98% by weight) to form a solution having a concentration of 0.5 g/100 ml. conc. sulfuric acid. At 30° C., the logarithmic viscosity of the polymer was measured for this solution.

$$\text{Logarithmic viscosity} = \frac{\ln \eta_{rel}}{c}$$

wherein $\eta_{rel}$ is $\dfrac{\text{Falling time in seconds of the sample solution}}{\text{Falling time in seconds of conc. sulfuric acid}}$ c is the amount in grams of the polymer dissolved in 100 ml. of conc. sulfuric acid, and 0.5.

In order that the resulting polymer will have good stretchability and spinnability, it should desirably have as high a logarithmic viscosity as possible.

The results of tests of the phthaloyl dichlorides obtained in the above examples are shown in Table 1 below.

Table 1

| Sample | Freezing point of IPC (°C.) | Relative viscosity of polymer | Freezing point of TPC (°C.) | Logarithmic viscosity of polymer |
|---|---|---|---|---|
| Example 1 | 43.80 | 3.83 | | |
| Example 2 | 43.80 | 3.82 | | |
| Comparative Example 1 | 43.68 | 3.41 | | |
| Ditto | 43.42 | 2.53 | | |
| Comparative Example 2 | 43.38 | 2.32 | | |
| Example 3 | | | 81.72 | 7.23 |
| Comparative Example 3 | | | 81.30 | 4.80 |
| Example 4 | 43.79 | 3.79 | | |
| Example 5 | | | 81.72 | 7.25 |
| Comparative Example 4 | 43.80 | 3.83 | | |

The results given in Table 1 clearly demonstrate that phthaloyl dichlorides produced from the α,α'-hexachloroxylenes obtained by the process of this invention are far more suitable as materials for polymers than those prepared from the α,α'-hexachloroxylenes produced by the methods of the comparative examples. It is also clear from the table that the suitabllity of phthaloyl dichlorides as materials for polymers has closely to do with their freezing points, and even slight differences in freezing points would greatly affect the degrees of polymerization of the resulting polymers.

What we claim is:

1. A batchwise or continuous process for producing isophthaloyl dichloride or terephthaloyl dichloride having a high purity which consists essentially of, in combination, (I) a first step of producing α,α,α,α',α',α'-hexachloroxylene by reacting a xylene compound selected from the group consisting of (i) xylene selected from meta-xylene and para-xylene and (ii) compounds resulting from the partial chlorination of the side-chain methyl groups of the xylene, with chloride under the irradiation of ultraviolet-containing rays, the reaction being carried out in the presence of, as a solvent, α,α,α,α',α',α'-hexachloroxylene added at the outset of the reaction; (a) the solvent being added in an amount of (1) from 0.3 to 15 times the weight of the starting xylene compound when the process is carried out in a batchwise manner or (2) in an amount of from 40 to 99% by weight of the reaction mixture when the process is carried out in a continuous manner; (b) the reaction temperature being (1) 80°–160° C. when the xylene compound is m-xylene or the compound resulting from the partial chlorination of its methyl groups or (2) 110°–160° C. when the xylene compound is p-xylene or the compound resulting from the partial chlorination of its methyl groups;

(II) a second step of producing isophthaloyl dichloride or terephthaloyl dichloride by reacting the α,α,α,α',α',α'-hexachloroxylene obtained in the first step with isophthalic acid or terephthalic acid, the α,α,α,α',α',α'-hexachloroxylene obtained in the first step being in an amount of 0.90 to 1.10 moles per mole of the isophthalic acid or terephthalic acid; and (III) a third step of purifying the isophthaloyl dichloride or terephthaloyl dichloride obtained in the second step by dissolving the isophthaloyl dichloride or terephthaloyl dichloride in 0.3 to 6 parts by weight, per part by weight of the phthaloyl dichloride, of a $C_6$–$C_{10}$ aliphatic hydrocarbon solvent, and cooling the solution to a temperature within the range of −20° C. +20° C. in the case of the isophthaloyl dichloride or to a temperature within the range of −20° C. to +50° C. in the case of the terephthaloyl dichloride thereby to recrystallize the phthaloyl dichloride.

2. The process of claim 1 wherein the xylene compound is meta-xylene or para-xylene.

3. The process of claim 1 wherein the reaction mixture obtained in the second step is distilled, and then recrystallized in the third step.

4. The process of claim 1 wherein the recrystallization in the third step is carried out in the absence of water.

* * * * *